United States Patent [19]

Jones

[11] Patent Number: 5,137,564
[45] Date of Patent: Aug. 11, 1992

[54] PYRIMIDINYL HERBICIDES

[75] Inventor: Graham P. Jones, Sawston, England

[73] Assignee: Schering Agrochemicals Limited, England

[21] Appl. No.: 557,915

[22] Filed: Jul. 25, 1990

[30] Foreign Application Priority Data

Jul. 27, 1989 [GB] United Kingdom ............... 8917222

[51] Int. Cl.$^5$ ............... C07D 239/30; C07D 239/48; C07D 239/52; A01N 43/54
[52] U.S. Cl. ............................. 71/92; 544/335; 544/334; 544/319; 544/326; 544/329; 544/242
[58] Field of Search ............. 71/92; 544/335, 334, 544/319, 326, 329, 242

[56] References Cited

U.S. PATENT DOCUMENTS 3,546,212 12/1970 Felix .................. 260/239.3

OTHER PUBLICATIONS

Hermann et al., Chemmical Abstracts, vol. 108, entry 37604z (1988).
Sauter et al., Chemical Abstracts, vol. 87, entry 151973s (1977).
Archer et al., Chemical Abstracts, vol. 87, entry 127254n (1977).
Malem et al., Chemical Abstracts, vol. 75, entry 5646y (1971).
Felix et al., Chemical Abstracts, vol. 74, entry 112062f (1971).
Archer et al., Chemical Abstracts, vol. 72, entry 100769n (1970).

Primary Examiner—John M. Ford
Attorney, Agent, or Firm—Ostrolenk, Faber, Gerb & Soffen

[57] ABSTRACT

Herbicidal benzylpyrimidine and benzyltriazine derivatives of the formula:

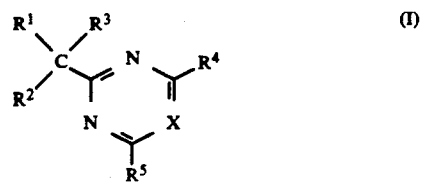

(I)

and salts thereof, where:

X is —CH= or —N=;

$R^1$ represents a substituted or unsubstituted phenyl group;

$R^2$ represents hydrogen, or a substituted or unsubstituted alkyl or aralkyl group;

$R^3$ represents cyano or a group —COOR or —CONRR', where R and R', which may be the same or different, each represent hydrogen, alkyl, alkenyl, alkynyl or aralkyl; and $R^4$ and $R^5$, which may be the same or different, each represent hydrogen, alkyl, alkoxy, amino or halogen, processes for their preparation, and compositions containing them.

21 Claims, No Drawings

PYRIMIDINYL HERBICIDES

This invention concerns new benzylpyrimidine and benzyltriazine derivatives having herbicidal activity, processes for their preparation, and compositions containing them.

In one aspect, the invention provides the benzylpyrimidine and benzyltriazine derivatives of the formula:

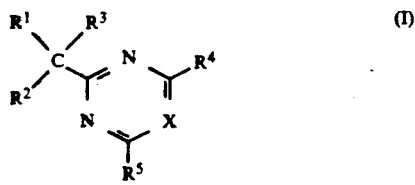

and salts thereof, where:

X represents —CH= or —N=;

$R^1$ represents a substituted or unsubstituted phenyl group;

$R^2$ represents hydrogen, or a substituted or unsubstituted alkyl or aralkyl group;

$R^3$ represents cyano or a group —COOR or —CONRR', where R and R', which may be the same or different, each represent hydrogen, alkyl, alkenyl, alkynyl or aralkyl; and $R^4$ and $R^5$, which may be the same or different, each represent hydrogen, alkyl, alkoxy, amino or halogen.

X is preferably —CH=.

When $R^1$ represents a substituted phenyl group, it is preferably substituted by one or more halogen atoms, e.g. fluorine, chlorine or bromine, nitro groups, substituted or unsubstituted amino groups (e.g. alkylamino, dialkylamino or acylamino groups, especially where the alkyl moiety has from 1 to 4 carbon atoms), cyano groups, alkyl or alkoxy groups of 1 to 4 carbon atoms (eg methyl, ethyl, methoxy or ethoxy), alkoxycarbonyl groups in which the alkyl moiety is of 1 to 4 carbon atoms (eg methoxycarbonyl or ethoxycarbonyl), or phenoxy groups.

When $R^2$, $R^3$, $R^4$ or $R^5$ represents or contains an alkyl group, that group is preferably of 1 to 6 carbon atoms, especially of 1 to 4 carbon atoms. When $R^2$ represents an alkyl group, it may if desired be substituted, for example by one or more halogen atoms (e.g. fluorine, chlorine or bromine), by alkoxy groups of 1 to 4 carbon atoms (e.g. methoxy or ethoxy), or by alkoxycarbonyl groups of 2 to 5 carbon atoms (e.g. methoxycarbonyl or ethoxycarbonyl).

When $R^2$, R or R' represents an aralkyl group, it is preferably a benzyl group.

When R or R' represents an alkenyl or alkynyl group, that group is preferably of 2 to 6 carbon atoms, for example vinyl, allyl or propargyl.

When $R^4$ or $R^5$ represents halogen, it is preferably fluorine, chlorine or bromine.

Specific preferred groups which $R^1$ may represent include phenyl, 2-chlorophenyl, 3-chlorophenyl, 4-chlorophenyl, 2,4-dichlorophenyl, 2-cyanophenyl, 3-trifluoromethylphenyl, 2-methylphenyl, 3-methylphenyl, 4-nitrophenyl, 4-aminophenyl, 2-methoxyphenyl, 3-methoxyphenyl, 4-methoxyphenyl, 2-methoxycarbonylphenyl and 2-ethoxycarbonylphenyl.

Specific preferred groups which $R^2$ may represent include hydrogen, methyl, ethyl, n-propyl, isopropyl, benzyl and ethoxycarbonylmethyl.

Specific preferred groups which $R^3$ may represent include methoxycarbonyl, ethoxycarbonyl, n-propoxycarbonyl, isopropoxycarbonyl, t-butoxycarbonyl, allyloxycarbonyl, propargyloxycarbonyl, benzyloxycarbonyl, cyano and carbamoyl.

Specific preferred groups which $R^4$ and $R^5$ may represent include methyl, methoxy and chloro.

In a particularly preferred group of compounds of formula I, X represents —CH=, $R^1$ represents phenyl, 3-chlorophenyl, 2-methoxyphenyl or 2-methoxycarbonylphenyl, $R^2$ represents hydrogen or methyl, $R^3$ represents cyano, methoxycarbonyl, ethoxycarbonyl, isopropoxycarbonyl or allyloxycarbonyl, and $R^4$ and $R^5$ both represent methoxy.

Specific preferred compounds according to the invention are those of the Examples provided hereinafter. Particular mention may, however, be made of methyl 2-(3-chlorophenyl)-2-(4,6-dimethoxypyrimidin-2-yl)propionate.

In another aspect, this invention provides a process for the preparation of a benzylpyrimidine or benzyltriazine derivative of formula I where $R^2$ represents hydrogen and $R^3$ represents cyano or a group —COOR as defined hereinbefore, in which a compound of the formula $R^1CH_2R^3$ where $R^1$ is as defined hereinbefore, and $R^3$ represents cyano or a group —COOR is reacted in the presence of a base, and in an appropriate solvent medium, with an alkylsulphonylpyrimidine of the formula:

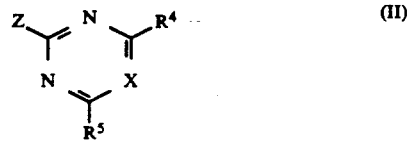

where Z is a leaving group, particularly chloro or a group of formula $R^aSO_2$— where $R^a$ is alkyl of 1 to 4 carbon atoms, and X, $R^4$ and $R^5$ are as defined hereinbefore to give the desired compound.

The base employed is preferably an alkali-metal hydride, for example sodium hydride, in a suitable solvent, for example dimethylformamide, and at temperature of from 0° C. to 25° C. Alternatively, the reaction may be carried out using butyllithium and di-isopropylamine at a temperature of about −70° C.

The compounds of formula I in which $R^3$ represents carbamoyl may be prepared by subjecting the corresponding compounds of formula I in which $R^3$ represents cyano to the action of a strong acid to give the desired compound.

The strong acid employed is preferably concentrated hydrochloric acid.

The compounds of formula I in which $R^2$ is other than hydrogen can be prepared from the corresponding compounds of formula I in which $R^2$ is hydrogen by reacting them with a suitable alkylating or aralkylating agent containing the group $R^2$, in the presence of a suitable base, by methods known per se.

The compounds of formula I are herbicidally-active against a wide range of broad-leaved and grassy weeds, but are comparatively safe to certain crop species. They may thus be of use as herbicides, and especially as selective herbicides, particularly in the control of a range of weeds in cereals or other crops, e.g. wheat, rice, barley, maize, soya beans, oilseed rape, cotton or sugar beet.

In another aspect, therefore, this invention provides a method of combating weeds at a locus infested or liable to be infested therewith which comprises applying thereto an effective amount of one or more compounds of formula I as defined hereinbefore. Preferred rates of application are from 0.01-2 kg/ha, especially from 0.05-1.5 kg/ha.

In a further aspect, this invention provides a herbicidal composition which comprises one or more compounds of formula I in association with a suitable carrier and/or surface active agent.

The compositions of the invention usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°-270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersingagent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds may be admixed with another pesticide, e.g. a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, phenmedipham, benzophenap, butachlor, chlomethoxyfen, dimepiperate, mefenacet, molinate, naproanilide, oxadiazon, piperophos, prometryne, pyrazoxyfen, pyrazosulfuron-ethyl, bensulfuron, simetryne, pyrazolate, pretilachlor, thiobencarb and pyributicarb.

The present compound may be applied to plants, the soil, land or aquatic areas, and particularly to a locus at which a crop is growing. The compounds are particularly active pre-emergence, but also have post-emergence activity.

The invention is illustrated by the following Examples in which Me=methyl, Et=ethyl, Pr=propyl, Bu=butyl, Ph=phenyl and Bz=benzyl.

EXAMPLE 1

Methyl (3-chlorophenyl)(4,6-dimethoxypyrimidin-2-yl) acetate

Sodium hydride (6.0 g of 80% in oil) was added to a stirred solution of methyl (3-chlorophenyl)acetate (36.8 g) and 4,6-dimethoxy-2-(methylsulphonyl)pyrimidine (42.6 g) in dimethylformamide (250 ml) with water bath cooling. The resulting suspension was stirred at room temperature for 18 hours. The mixture was then poured onto water (1.5 l) and the resulting oil was extracted into ether. The combined extracts were washed with saturated sodium chloride solution, dried over magnesium sulphate, and evaporated to give a yellow oil, which was purified by chromatography to give 42.3 g of the desired product as a colourless oil.

EXAMPLE 2

Ethyl (2-Methylphenyl)(4,6-dimethoxypyrimidin-2-yl)acetate n-Butyllithium (10 ml of 2N solution in pentane) was added dropwise to a stirred solution of di-isopropylamine (2.0 g) in dry tetrahydrofuran (40 ml) under nitrogen at −10° C. After stirring at this temperature for 15 minutes, the solution was cooled to −75° C., and a solution of ethyl (2-methylphenyl)acetate (3.56 g) in tetrahydrofuran (20 ml) was added dropwise. After stirring at −75° C. for one hour, 4,6-dimethoxy-2-(methylsulphonyl)pyrimidine (4.36 g) was added in one portion, and the resulting suspension was allowed to warm slowly to room temperature before stirring overnight. The reaction mixture was then poured onto water (400 ml) and the resulting oil was extracted into ether (2×150 ml). The combined extracts were washed with saturated sodium chloride solution, dried over magnesium sulphate and evaporated to give a yellow oil which was purified by chromatography to give 3.8 g of the desired product as a colourless oil.

EXAMPLES 3–23

The following compounds of formula I where X is —CH= and $R^2$ is hydrogen were prepared by methods analogous to that of Example 1:

| Ex | $R^1$ (Ph subst:) | $R^3$ | $R^4$ | $R^5$ | M Pt (°C.) |
|---|---|---|---|---|---|
| 3 | H | COOMe | OMe | OMe | 47–49 |
| 4 | 3-Me | COOEt | Me | Me | 96–97 |
| 5 | 4-NO$_2$ | COOEt | Me | Me | Oil |
| 6 | 4-NH$_2$ | COOEt | Me | Me | 143–144 |
| 7 | 4-Cl | COOMe | OMe | OMe | 76–77 |
| 8 | 3-Cl | COOMe | Me | Me | 92–95 |
| 9 | H | COOt-Bu | Me | Me | 93–94 |
| 10 | 2-Cl | COOMe | OMe | OMe | 73–75 |
| 11 | 3-OMe | COOMe | OMe | OMe | Oil |
| 12 | 3-Cl | COOBz | OMe | OMe | 58–62 |
| 13 | H | COOEt | OMe | OMe | Oil |
| 14 | 2,4-diCl | COOMe | OMe | OMe | Oil |
| 15 | 4-OMe | COOMe | OMe | OMe | 72–73 |
| 16 | H | COOn-Pr | OMe | OMe | Oil |
| 17 | 3-CF$_3$ | COOMe | OMe | OMe | Oil |
| 18 | 3-Me | COOEt | OMe | OMe | Oil |
| 19 | 3-Cl | COOEt | OMe | OMe | Oil |
| 20 | H | COOallyl | OMe | OMe | Oil |
| 21 | H | COOMe | Me | Me | 130–131 |
| 22 | 3-Cl | COOEt | Cl | OMe | Oil |
| 23 | 3-Cl | COOMe | Cl | OMe | Oil |

EXAMPLES 24–30

The following compounds of formula I where X is —CH= and $R^2$ is hydrogen were prepared by methods analogous to that of Examples 2:

| Ex | $R^1$ (Ph subst:) | $R^3$ | $R^4$ | $R^5$ | M Pt (°C.) |
|---|---|---|---|---|---|
| 24 | 2-OMe | COOMe | OMe | OMe | 98–99 |
| 25 | H | COOi-Pr | OMe | OMe | Oil |
| 26 | 2-OMe | COOEt | OMe | OMe | 71–72 |
| 27 | 2-COOMe | COOMe | OMe | OMe | 124–125 |
| 28 | H | COOMe | Cl | OMe | 56–59 |
| 29 | H | COOEt | Cl | OMe | Oil |
| 30 | H | COOpropargyl | OMe | OMe | Oil |

EXAMPLE 31

Methyl 2-(3-chlorophenyl)-2-(4,6-dimethoxypyrimidin-2-yl)propionate

Sodium hydride (0.6 g of 80% in oil) was added to a stirred solution of the product of Example 1 (6.29 g) in dimethylformamide (40 ml) and the mixture was stirred at room temperature for 40 minutes. Dimethyl sulphate (2.52 g) was added dropwise, and the mixture was stirred for 3 hours at room temperature before being poured onto water (250 ml). The resulting oil was extracted into ether, and the combined extracts were washed with saturated sodium chloride solution, dried over magnesium sulphate and evaporated to give a yellow oil, which was purified by chromatography to give 4.4 g of the desired product as a colourless oil.

EXAMPLES 32–41

The following compounds of formula I where X is —CH= and $R^4$ and $R^5$ are both methoxy were prepared by methods analogous to those of Example 31:

| Ex | $R^1$ (Ph subst:) | $R^2$ | $R^3$ | M Pt (°C.) |
|---|---|---|---|---|
| 32 | H | Me | COOMe | 66–67 |
| 33 | H | CH$_2$COOEt | COOMe | Oil |
| 34 | 3-Cl | CH$_2$COOEt | COOMe | 99–100 |
| 35 | H | Bz | COOMe | 105–108 |
| 36 | H | Et | COOMe | Oil |
| 37 | H | n-Pr | COOMe | Oil |
| 38 | 2-Cl | Me | COOEt | Oil |
| 39 | H | i-Pr | COOMe | Oil |
| 40 | 2-OMe | Me | COOEt | Oil |
| 41 | H | Me | COOpropargyl | Oil |

EXAMPLES 42–47

The following compounds of formula I where X is —CH=, $R^4$ is chloro and $R^5$ is methoxy were prepared by methods analogous to that of Example 31:

| Ex | $R^1$ (Ph subst:) | $R^2$ | $R^3$ | M Pt (°C.) |
|---|---|---|---|---|
| 42 | H | Me | COOEt | Oil |
| 43 | 3-Cl | Me | COOEt | Oil |
| 44 | 3-Cl | CH$_2$COOEt | COOEt | Oil |
| 45 | H | Me | COOMe | Oil |
| 46 | 2-Cl | Me | COOMe | Oil |
| 47 | 3-Cl | CH$_2$COOEt | COOMe | Oil |

EXAMPLE 48

(3-Chlorophenyl)(4,6-dimethoxypyrimidin-2-yl)acetonitrile

Sodium hydride (6.0 g of 80% in oil) was added portionwise to a stirred solution of 4,6-dimethoxy-2-(methylsulphonyl)pyrimidine (21.8 g) and (3-chlorophenyl)acetonitrile (15.1 g) in dry dimethylformamide (150 ml) at 5° C. The mixture was stirred at 10° C. for 30 minutes, and then at room temperature for 3 hours. The resulting suspension was poured into water (1.2 l) and the oil was extracted into ether. The combined extracts were washed with saturated sodium chloride solution, dried over magnesium sulphate and evaporated to give an orange oil, which was purified by chromatography to give 26.3 g of the desired product as a pale yellow oil.

EXAMPLES 49-55

The following compounds of formula I where X is —CH=, $R^2$ represents hydrogen and $R^3$ represents cyano were prepared by methods analogous to that of Example 48:

| Ex | $R^1$ (Ph subst:) | $R^4$ | $R^5$ | M Pt (°C.) |
|----|-------------------|-------|-------|------------|
| 49 | H | OMe | OMe | 52-53 |
| 50 | 2-CN | OMe | OMe | 113-114 |
| 51 | 2-OMe | OMe | OMe | 95-96 |
| 52 | 3-CF$_3$ | OMe | OMe | 53-56 |
| 53 | 2-Cl | OMe | OMe | 69-72 |
| 54 | H | Me | Me | 73-76 |
| 55 | 2-Me | Me | Me | 129-133 |

EXAMPLE 56

2-(3-Chlorophenyl)-2-(4,6-dimethoxypyrimidin-2-yl)acetamide

The product of Example 48 (5.0 g) was added to concentrated hydrochloric acid (25 ml) at room temperature, and the mixture was stirred for 4 hours. The resulting solution was poured onto water (100 ml), and extracted with ethyl acetate (3×100ml). The combined extracts were washed with saturated sodium chloride solution, dried over magnesium sulphate, and evaporated to give a yellow oil which was purified by chromatography to give 1.4 g of a pale yellow solid. This was crystallised from ethyl acetate to give 0.9 g of the desired product as a white solid, mp 118°-119° C.

EXAMPLES 57-59

The following compounds of formula I in which X is —CH=, $R^2$ represents hydrogen, and $R^3$ represents carbamoyl were prepared by methods analogous to that of Example 56:

| Ex | $R^1$ (Ph subst:) | $R^4$ | $R^5$ | M Pt (°C.) |
|----|-------------------|-------|-------|------------|
| 57 | H | OMe | OMe | 119-120 |
| 58 | 3-CF$_3$ | OMe | OMe | 101-103 |
| 59 | 2-Cl | OMe | OMe | 124-127 |

EXAMPLE 60

2-(3-Chlorophenyl)-2-(4,6-dimethoxypyrimidin-2-yl)propiononitrile

Sodium hydride (0.83 g of 80% in oil) was added to a stirred solution of the product of Example 48 (8.0 g) in dimethylformamide at room temperature. Dimethyl sulphate (3.5 g) was then added, and the mixture was stirred at room temperature for 4 hours. The mixture was poured onto water (250 ml), and the oil was extracted into ethyl acetate. The combined extracts were dried over magnesium sulphate, and evaporated to give an orange liquid, which was purified by chromatography to give 5.2 g of the desired product as a white solid, mp 89°-93° C.

EXAMPLE 61

The following compound of formula I where X is —CH= and $R^3$ represents cyano was prepared by a method analogous to that of Example 60:

| Ex | $R^1$ (Ph subst:) | $R^2$ | $R^4$ | $R^5$ | M Pt (°C.) |
|----|-------------------|-------|-------|-------|------------|
| 61 | H | Me | OMe | OMe | 60-63 |

EXAMPLES 62-63

The following compounds of formula I where X represents —N=, and $R^4$ and $R^5$ both represent methoxy were prepared by methods analogous to that of Example 2:

| Ex | $R^1$ (Ph subst:) | $R^2$ | $R^3$ | M Pt (°C.) |
|----|-------------------|-------|-------|------------|
| 62 | 3-Cl | H | COOEt | Oil |
| 63 | H | H | COOpropargyl | Oil |

HERBICIDAL EXAMPLE A (Pre-Emergence)

Seeds of the weed species listed below were sown in anodised aluminum pans 19 cm long×9.5 cm wide × 6 cm deep, containing sterilized sandy loam. They were watered and then sprayed with the compounds of the Examples listed below formulated as a solution/suspension in 1:1 by volume of acetone and the wetting agent polyoxyethylene (20 mols) monolaurate solution (2 g per liter).

The concentration of each test compound and volume of application were calculated to give the desired rate of application of the compound in 450 litres per hectare. After 3 to 4 weeks growth in the controlled environment room (20° C.; 75%-95% relative humidity; 14 hours per day artificial illumination) the plants were visually assessed for any herbicidal response.

All differences from an untreated control were scored accordingly to an index where 0=no effect, 1=1%-24% effect, 2=25%-69% effect, 3=70%-89% effect and 4=90%-100% effect. In the table below, the are used to denote the plant species:

a - *Polygonum lapathifolium* (Pale persicaria)
b - *Galium aparine* (cleavers)
c - *Chrysanthemum segetum* (corn marigold)
d - *Alopecurus myosuroides* (blackgrass)
e - *Agropyron repens* (Couchgrass)
f - *Avena fatua* (wild oat)
g - *Abutilon theophrasti* (velvetleaf)
h - *Cyperus esculentus* (yellow nutsedge)
i - *Pharbitis purpurea* (morningglory)
j - *Echinochloa crus-galli* (barnyardgrass)
k - *Setaria viridis* (green foxtail)
l - *Solanum nigrum* (black nightshade)

The results obtained were as follows:

| Ex | Kg/ha | a | b | c | d | e | f | g | h | i | j | k | l |
|----|-------|---|---|---|---|---|---|---|---|---|---|---|---|
| 16 | 1.0 | 2 | 4 | 0 | 4 | 4 | 2 | 2 | 4 | 0 | 3 | 3 | 4 |
| 19 | 1.0 | 0 | 4 | 0 | 2 | 4 | 2 | 4 | 2 | 1 | 3 | 3 | 4 |
| 20 | 1.0 | 4 | 4 | 0 | 3 | 4 | 2 | 2 | 4 | 0 | 4 | 4 | 4 |
| 25 | 1.0 | 2 | 4 | 0 | 3 | 4 | 2 | 1 | 3 | 0 | 3 | 3 | 4 |
| 26 | 1.0 | 3 | 4 | 4 | 2 | 4 | 0 | 2 | 2 | 2 | 3 | 2 | 4 |
| 27 | 1.0 | 3 | 4 | 3 | 2 | 4 | 2 | 2 | 3 | 0 | 2 | 2 | — |
| 31 | 1.0 | 4 | 4 | 0 | 2 | 4 | 2 | 2 | 4 | 1 | 3 | 3 | 4 |
| 51 | 1.0 | 2 | 3 | 4 | 0 | 0 | 0 | 3 | 0 | 3 | 3 | 0 | 4 |

HERBICIDAL EXAMPLE B (Post-Emergence)

Seeds of the plant species listed below were sown in anodised aluminum pans, 19 cm long×9.5 cm×6 cm deep, containing sterilised sandy loam. They were then watered and placed in a controlled environment room (20° C.; 75%-95% relative humidity; 14 hours per day artificial illumination). Fourteen or twenty one days after sowing (depending on the species but when most plants had 2 to 3 true leaves) the seedlings received a foliar spray of the compounds of the Examples listed below, formulated as a solution/suspension in 1:1 by volume of acetone and the wetting agent polyoxyethylene (20 mols) monolaurate solution (2 g per liter).

The concentration of each test compound was calculated to give the desired rate of application of the compound in 450 liters per hectare. After 2 to 3 weeks growth in the controlled environment room the plants were visually assessed for any herbicidal response.

All differences from an untreated control were scored according to an index where 0=no effect, 1=1%-24% effect, 2=25%-69% effect, 3=70%-89% effect and 4=90%-100% effect. In the table below, the letters used denote the same plant species as in Herbicidal Example A:

The results obtained were as follows:

| Ex | Kg/ha | a | b | c | d | e | f | g | h | i | j | k | l |
|----|-------|---|---|---|---|---|---|---|---|---|---|---|---|
| 16 | 1.0 | 2 | 3 | 0 | 4 | 2 | 2 | 0 | 2 | 0 | 2 | 2 | 4 |
| 19 | 1.0 | 3 | 4 | 0 | 3 | 2 | 3 | 0 | 2 | 1 | 4 | 3 | — |
| 20 | 1.0 | 2 | 3 | 0 | 3 | 2 | 3 | 2 | 3 | 0 | 2 | 2 | — |
| 25 | 1.0 | 0 | 2 | 0 | 2 | 2 | 2 | 0 | 0 | 0 | 0 | 2 | 4 |
| 26 | 1.0 | 0 | 2 | 4 | 2 | 0 | 2 | 1 | 2 | 1 | 2 | 0 | 4 |
| 27 | 1.0 | 2 | 2 | 2 | 2 | 0 | 2 | 2 | 0 | 0 | 0 | 0 | 3 |
| 31 | 1.0 | 2 | 4 | 0 | 2 | 2 | 2 | 0 | 2 | 0 | 2 | 0 | — |
| 51 | 1.0 | 2 | 2 | 1 | 0 | 0 | 2 | 3 | 2 | 0 | 2 | 2 | 3 |

I claim:

1. A benzylpyrimidine of the formula:

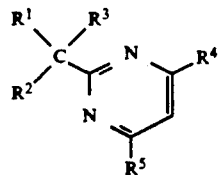

(I)

and salts thereof, where:

$R^1$ represents phenyl (optionally substituted by at least one halogen atom, nitro group, amino group, cyano group, alkyl or alkoxy group of 1 to 4 carbon atoms, alkyoxycarbonyl group of 2 to 5 carbon atoms, or phenoxy group);

$R^2$ represents hydrogen, alkyl of 1 to 6 carbon atoms (optionally substituted by at least one halogen atom, alkoxy group of 1 to 4 carbon atoms, or alkoxycarbonyl group of 2 to 5 carbon atoms), or benzyl;

$R^3$ represents a group —COOR, or —CONRR', where R and R', which may be the same or different, each represent hydrogen, alkyl of 1 to 6 carbon atoms, alkenyl or alkynyl of 2 to 6 carbon atoms, or benzyl; and $R^4$ and $R^5$, which may be the same of different, each represent hydrogen, alkyl or alkoxy of 1 to 6 carbon atoms, amino or halogen.

2. A compound according to claim 1 in which $R^1$ represents 2-chlorophenyl, 3-chlorophenyl, 4-chlorophenyl, 2,4-dichlorophenyl, 2-cyanophenyl, 3-trifluoromethylphenyl, 2-methylphenyl, 3-methylphenyl, 4-nitrophenyl, 4-aminophenyl, 2-methoxyphenyl, 3-methoxyphenyl, 4-methoxyphenyl, 2-methoxycarbonylphenyl or 2-ethoxycarbonylphenyl.

3. A compound according to claim 1 in which $R^2$ represents alkyl of 1 to 6 carbon atoms (optionally substituted by one or more halogen atoms, alkoxy groups of 1 to 4 carbon atoms, or alkoxycarbonyl groups of 2 to 5 carbon atoms), or benzyl.

4. A compound according to claim 3 in which $R^2$ represents methyl, ethyl, n-propyl, isopropyl or ethoxycarbonylmethyl.

5. A compound according to claim 1 in which $R^3$ represents a group —COOR where R is alkyl of 1 to 6 carbon atoms, alkenyl of 2 to 6 carbon atoms, or alkynyl of 2 to 6 carbon atoms.

6. A compound according to claim 6 in which $R^3$ represents methoxycarbonyl, ethoxycarbonyl, n-propoxycarbonyl, isopropoxycarbonyl, t-butoxycarbonyl, allyloxycarbonyl, propargyloxycarbonyl, or benzyloxycarbonyl.

7. A compound according to claim 1 in which $R^4$ and $R^5$ each represent chlorine, methyl or methoxy.

8. Methyl 2-(3-chlorophenyl)-2-(4,6-dimethoxypyrimidin-2-yl)propionate.

9. A compound according to claim 1 in which $R^1$ is phenyl, 3-chlorophenyl, 2-methoxyphenol or 2-methoxycarbonylphenyl, $R^2$ is hydrogen or methyl, $R^3$ is cyano, methoxycarbonyl, ethoxycarbonyl, isopropoxycarbonyl or allyloxycarbonyl, and $R^4$ and $R^5$ both represent methoxy.

10. A compound according to claim 9 in which $R^2$ is hydrogen.

11. A herbicidal composition which comprises an effective amount of at least one compound according to claim 1 in association with a suitable carrier and/or surface active agent.

12. A herbicidal composition which comprises an effective amount of at least one compound according to claim 3 in association with a suitable carrier and/or surface active agent.

13. A herbicidal composition which comprises an effective amount of at least one compound according to claim 5 in association with a suitable carrier and/or surface active agent.

14. A herbicidal composition which comprises an effective amount of at least one compound according to claim 9 in association with a suitable carrier and/or surface active agent.

15. A herbicidal composition which comprises an effective amount of at least one compound according to claim 10 in association with a suitable carrier and/or surface active agent.

16. A benzylpyrimidine of the formula:

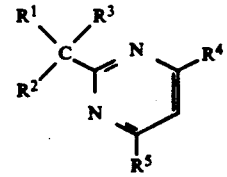

(I)

and salts thereof, where:

$R^1$ represents phenyl (optionally substituted by at least one halogen atom, nitro group, amino group, cyano group, alkyl or alkoxy group of 1 to 4 carbon atoms, alkyoxycarbonyl group of 2 to 5 carbon atoms, or phenoxy group);

$R^2$ represents alkyl of 1 to 6 carbon atoms (optionally substituted by at least one halogen atom, alkoxy group of 1 to 4 carbon atoms, or alkoxycarbonyl group of 2 to 5 carbon atoms), or benzyl;

$R^3$ represents cyano;

$R^4$ and $R^5$, which may be the same of different, each represent hydrogen, alkyl or alkoxy of 1 to 6 carbon atoms, amino or halogen.

17. A herbicidal composition which comprises an effective amount of at least one compound according to claim 16 in association with a suitable carrier and/or surface active agent.

18. A benzylpyrimidine of the formula:

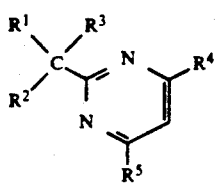

and salts thereof, where:

$R^1$ represents phenyl substituted by at least one nitro group, amino group, cyano group, alkyl or alkoxy group of 2 to 5 carbon atoms, or phenoxy group;

$R^2$ represents hydrogen;

$R^3$ represents cyano; and $R^4$ and $R^5$, which may be same or different, each represent hydrogen, alkoxy of 1 to 6 carbon atoms, amino or halogen.

19. A herbicidal composition which comprises an effective amount of at least one compound according to claim 18 in association with at suitable carrier and/or surface active agent.

20. A benzylpyrimidine of the formula:

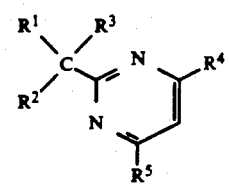

and salts thereof, where:

$R^1$ represents phenyl substituted by at least one nitro group, amino group, cyano group, alkyl or alkoxy group of 1 to 4 carbon atoms, alkyoxycarbonyl group of 2 to 5 carbon atoms, or phenoxy group;

$R^2$ represents hydrogen;

$R^3$ represents cyano; and $R^4$ and $R^5$, which may be the same of different, each represent hydrogen, alkyl or alkoxy of 1 to 6 carbon atoms, amino or halogen.

21. A herbicidal composition which comprises an effective amount of at least one compound according to claim 20 in association with a suitable carrier and/or surface active agent.

* * * * *